United States Patent
Alsina-Fernandez et al.

(10) Patent No.: US 9,688,736 B2
(45) Date of Patent: Jun. 27, 2017

(54) COMPOUND FOR TREATMENT OF SEVERE HYPOGLYCEMIA

(71) Applicant: Eli Lilly and Company, Indianapolis, IN (US)

(72) Inventors: Jorge Alsina-Fernandez, Indianapolis, IN (US); Robert Chadwick Cummins, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/103,169

(22) PCT Filed: Dec. 11, 2014

(86) PCT No.: PCT/US2014/069646
§ 371 (c)(1),
(2) Date: Jun. 9, 2016

(87) PCT Pub. No.: WO2015/094878
PCT Pub. Date: Jun. 25, 2015

(65) Prior Publication Data
US 2016/0311883 A1    Oct. 27, 2016

Related U.S. Application Data

(60) Provisional application No. 61/917,658, filed on Dec. 18, 2013.

(51) Int. Cl.
| | | |
|---|---|---|
| *A61K 38/00* | (2006.01) | |
| *A61K 38/26* | (2006.01) | |
| *A61K 38/16* | (2006.01) | |
| *C07K 14/605* | (2006.01) | |
| *C07K 7/00* | (2006.01) | |

(52) U.S. Cl.
CPC ............ *C07K 14/605* (2013.01); *A61K 38/00* (2013.01)

(58) Field of Classification Search
CPC ........ A61K 38/00; A61K 38/26; A61K 38/16; C07K 14/605; C07K 7/086
USPC ................. 514/7.2, 11.7, 21.3; 530/308, 324
See application file for complete search history.

(56) References Cited

U.S. PATENT DOCUMENTS

| 8,450,270 B2 * | 5/2013 | Dimarchi ............. C07K 14/605 514/11.7 |
|---|---|---|
| 2010/0190699 A1 | 7/2010 | Dimarchi |
| 2011/0190200 A1 | 8/2011 | Dimarchi et al. |
| 2011/0288003 A1 | 11/2011 | Dimarchi et al. |
| 2012/0178670 A1 | 7/2012 | Riber et al. |
| 2012/0322725 A1 | 12/2012 | Dimarchi et al. |
| 2013/0116172 A1 | 5/2013 | Dimarchi et al. |
| 2016/0199451 A1 * | 7/2016 | Jung ...................... A61K 38/22 424/179.1 |

FOREIGN PATENT DOCUMENTS

| WO | 2008086086 A2 | 7/2008 |
|---|---|---|
| WO | 2009099763 A1 | 8/2009 |
| WO | 2009155257 A1 | 12/2009 |
| WO | 2009155258 A2 | 12/2009 |
| WO | 2011006497 A1 | 1/2010 |
| WO | 2010071807 A1 | 6/2010 |
| WO | 2011088837 A1 | 7/2011 |
| WO | 2011094337 A1 | 8/2011 |
| WO | 2011143208 A1 | 11/2011 |
| WO | 2011143209 A1 | 11/2011 |
| WO | 2011160633 A1 | 12/2011 |
| WO | 2011163012 A2 | 12/2011 |
| WO | 2011163473 A1 | 12/2011 |
| WO | 2012088379 A2 | 6/2012 |
| WO | 2012098462 A1 | 7/2012 |
| WO | 2012130866 A1 | 10/2012 |

OTHER PUBLICATIONS

Joseph Chabenne et al: "A glucagon analog chemically stabilized for immediate treatment of life-threatening hypoglycemia", Molecular Metabolism, vol. 3, No. 3, Jun. 1, 2014, pp. 293-300, XP55173894, ISSN: 2212-8778, DOI:10.1016/j.molmet.2014.01. 006, p. 297, paragraph 3.5—p. 299, paragraph 3.9.

Joseph Chabenne et al: "Optimization of the Native Glucagon Sequence for Medicinal Purposes Corresponding Author", Journal of Diabetes Science and Technology Volume Diabetes Technology Society, Nov. 1, 2010, XP55173893.

\* cited by examiner

*Primary Examiner* — Julie Ha
(74) *Attorney, Agent, or Firm* — Alejandro Martinez

(57) ABSTRACT

A peptide compound useful in the treatment of hypoglycemia is described.

8 Claims, No Drawings

COMPOUND FOR TREATMENT OF SEVERE HYPOGLYCEMIA

The present invention relates to a compound with improved solubility and physical and chemical stabilities over human glucagon for use in treating diabetes and/or obesity.

Human glucagon, which has the following amino acid sequence: His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1), is a 29 amino acid peptide hormone produced in the pancreas. When blood glucose begins to fall, glucagon signals the liver to break down stored glycogen into glucose for release into the bloodstream, causing blood glucose level to rise.

In a subject with diabetes, hypoglycemia can arise as a side effect of diabetes treatment. In addition, the natural glucagon response to hypoglycemia in diabetics may be impaired, making it harder for glucose levels to return to the normal range. If left untreated, severe or acute hypoglycemia can cause serious issues such as seizures, unconsciousness, brain damage, or even death.

Administration of glucagon is an established therapy for treating acute hypoglycemia. Emergency glucagon administration can restore normal glucose levels within minutes of administration. Glucagon prepared for administration, however, has several problems. In aqueous buffers at or near physiological pH, glucagon has poor solubility. When formulated at low or high pH, glucagon also demonstrates poor chemical stability and poor physical stability such as gelation and soluble aggregate formation. To minimize these problems, current commercial glucagon products are provided as a lyophilized powder with instructions to reconstitute at the time of administration. In an emergency situation, reconstituting a lyophilized powder is burdensome and inconvenient. Thus, it is desirable to provide a compound for therapeutic use that maintains the biological performance of human glucagon under physiological conditions while also exhibiting sufficient aqueous solubility, chemical stability and physical stability under non-physiological conditions.

Glucagon analogs with amino acid substitutions to improve solubility and stability in acidic and physiological pH buffers are disclosed in WO2008086086. There is still a need for a compound that maintains the biological performance of human glucagon under physiological conditions while also exhibiting sufficient solubility and chemical and physical stabilities under non-physiological conditions.

Accordingly, the present invention seeks to provide a compound which maintains wild-type glucagon activity but also exhibit sufficient solubility as well as chemical and physical stability. The present invention also provides a compound which is suitable for pump and/or emergency administration. In addition, the present invention provides a compound that can be administered in combination with a fast-acting insulin analog in a dual-chamber pump to provide closed-loop glycemic control.

The present invention provides a compound comprising the amino acid sequence
Tyr-Ser-His-Gly-Thr-Phe-Thr-Ser-Asp-Val-Ser-Lys-Tyr-Leu-Asp-(Aib)-Lys-Lys-Ala-Ala-Glu-Phe-Val-Ala-Trp-Leu-Leu-Glu-Glu (SEQ ID NO: 2). The present invention also provides a compound consisting of the amino acid sequence
Tyr-Ser-His-Gly-Thr-Phe-Thr-Ser-Asp-Val-Ser-Lys-Tyr-Leu-Asp-(Aib)-Lys-Lys-Ala-Ala-Glu-Phe-Val-Ala-Trp-Leu-Leu-Glu-Glu (SEQ ID NO: 2). Unexpectedly, it has been found that the compound of the present invention exhibits increased aqueous solubility, increased chemical stability, and reduced fibrillation as compared to human glucagon in aqueous solution. In addition, the compound of the present invention demonstrates enhanced solubility at pH near 8. The compound of the present invention also provides similar activity as human glucagon—e.g., potency, time of action, and selectivity at the glucagon receptor as compared to human glucagon. Thus, the compound of the present invention is suitable to treat hypoglycemia, including severe or acute hypoglycemia. The improved properties of the compound of the present invention also allow for the preparation of glucagon in aqueous solutions for pump administration and severe hypoglycemia treatment.

The present invention further provides a method of treating hypoglycemia in a subject comprising administering a compound comprising the amino acid sequence of SEQ ID NO: 2. The present invention also provides a method of treating hypoglycemia in a subject comprising administering a compound consisting of the amino acid sequence of SEQ ID NO:2. The present invention a further provides a compound comprising the amino acid sequence of SEQ ID NO: 2 for use in therapy. The present invention also provides a compound consisting of the amino acid sequence of SEQ ID NO: 2 for use in therapy. The present invention also provides a compound comprising the amino acid sequence of SEQ ID NO: 2 for use in the treatment of hypoglycemia. The present invention also provides a compound consisting of the amino acid sequence of SEQ ID NO: 2 for use in the treatment of hypoglycemia. The present invention provides a compound comprising the amino acid sequence of SEQ ID NO: 2 for use in the manufacture of a medicament for the treatment of hypoglycemia. The present invention also provides a compound consisting of the amino acid sequence of SEQ ID NO: 2 for use in the manufacture of a medicament for the treatment of hypoglycemia.

The present invention provides a pharmaceutical composition comprising a compound comprising an amino acid sequence of SEQ ID NO: 2 and a pharmaceutically acceptable buffer. The present invention also provides a pharmaceutical composition comprising a compound consisting of the amino acid sequence of SEQ ID NO: 2 and a pharmaceutically acceptable buffer. The pharmaceutical composition is preferably an aqueous solution. As used herein, the term "pharmaceutically acceptable buffer" is understood to encompass any of the standard pharmaceutical buffers known to those skilled in the art. Pharmaceutically acceptable buffers for parenteral administration include, for example, physiological saline, phosphate-buffered saline, citrate-buffered saline, tris-buffered saline and histidine-buffered saline. Standard pharmaceutical formulation techniques may be employed such as those described in Remington's Pharmaceutical Sciences, Mack Publishing Company, Easton, Pa. Standard pharmaceutical formulation techniques may be employed such as those described in Remington's Pharmaceutical Sciences, Mack Publishing Company, Easton, Pa.

The compound of the present invention can be administered using any standard route of administration, such as parenterally, intravenously, subcutaneously, intramuscularly, or transdermally. In an embodiment, the compound of the present invention is administered subcutaneously or intramuscularly.

The pharmaceutical composition can have a pH that is physiologically acceptable. In an embodiment, the pharmaceutical composition can have a pH ranging from about 4 to about 8. More preferably, the pharmaceutical composition can have a pH of about 8.

A dose for the compound of the present invention can range from about 0.01 mg to about 100 mg. The dose can range from about 0.01 mg to about 10 mg. The dose can also range from about 0.1 mg to about 3 mg. In addition, the dose can range from about 0.01 mg to about 0.03 mg.

The compound of the present invention can be provided as part of a kit. In an embodiment, the kit is provided with a device for administering the compound to a human subject. More preferably, the kit comprises a syringe and needle for administering the compound. Most preferably, the compound is pre-formulated in aqueous solution within the syringe.

The compound of the present invention can also be used in a pump system, such as an insulin pump or a bi-hormonal (e.g., insulin-glucagon) pump system.

As used herein, the term "effective amount" or "therapeutically effective amount" is understood to mean an amount that produces a desired therapeutic effect without causing unacceptable side effects when administered to a subject. For example, an "effective amount" of the disclosed compound of the present invention is the quantity that would result in greater control of blood glucose concentration than in the absence of treatment. An "effective amount" of a compound of the present invention administered to a subject may depend on the type and severity of the disease and on the characteristics of the subject including, without limitation, general health, age, sex, body weight, tolerance to drugs, and the severity of inability to regulate blood glucose.

As used herein, the term "treating" is understood to mean amelioration of the symptoms associated with a specific disorder or condition, such as hypoglycemia.

The amino acid sequences of the present invention contain the standard single letter or three letter codes for the twenty naturally occurring amino acids. Additionally, "Aib" is alpha amino isobutyric acid.

As used herein, "fibrillation" refers to gelation and soluble aggregate formation observed when glucagon is formulated at low or high pH.

Example 1: Peptide Synthesis

The compound of SEQ ID NO: 2 is generated by solid-phase peptide synthesis on a Protein Technologies Inc. Symphony. Synthesis (0.125 mmols scale) is performed on Fmoc-Glu(OtBu)-Wang polystyrene resin (Advanced ChemTech) with substitution approximately 0.9 mmol/g. The synthesis is performed using the Fmoc main-chain protecting group strategy. Amino acid side-chain derivatives used are: Asp(O-tert-butyl, OtBu), Gln(Trityl, Trt), Glu(OtBu), His(Trt), Lys(tert-butoxy-carbonyl, Boc), Ser(OtBu), Thr(OtBu), Trp(Boc), and Tyr(OtBu). Coupling is carried out with approximately 10 equivalents of amino acid activated with diisopropylcarbodiimide (DIC) and hydroxybenzotriazole (HOBt) (1:1:1 molar ratio) in dimethylformamide (DMF). Coupling is carried out for 90 minutes to 4 hours at room temperature.

Concomitant cleavage from the resin and side chain protecting group removal is carried out in a solution containing trifluoroacetic acid (TFA): triisopropylsilane : 1,2-ethanedithiol: water:thioanisole 90:4:2:2:2 (v/v) for 2 h at room temperature. The solution is filtered and peptide is precipitated with cold diethyl ether and centrifuged at 4000 rpm for 3 min (cold ether washing repeated for three times). Crude peptide is redissolved in 100-150 mL of water containing 10% acetic acid and purified on a $C_{18}$ reversed-phase high performance liquid chromatography (HPLC) column (typically a Waters SymmetryPrep 7 um, 19×300 mm) at a flow rate of 18 mL/min Sample is eluted with a linear AB gradient of 22 to 55% B over 100 minutes where A=0.05% TFA/water and B=0.04% TFA/acetonitrile. Product generally elutes at about 32-35% acetonitrile. Peptide purity and molecular weight is confirmed on an Agilent 1100 Series liquid chromatography-mass spectrometry (LC-MS) system with a single quadrupole MS detector. Analytical HPLC separation is done on a Waters SymmetryShield RP18, 3.5 micron, 4.6 mm×100 mm column with a linear AB gradient of 10 to 100% B over 15 minutes in which A=0.05% TFA/$H_2O$ and B=0.04% TFA/40% water/60% acetonitrile and the flow rate is 0.7 mL/min (wavelength of 220 ηm). The peptide analogue is purified to >95% purity and is confirmed to have molecular weight corresponding to the calculated value within 1 atomic mass unit (amu).

The TFA salt is converted to the acetate salt using AG 1-X8 Resin (Bio-RAD, acetate form, 100-200 mesh, 3.2 meq/dry g, moisture content 39-48% by wt) (anion exchange resin). For example, 464 mg peptide is dissolved in 120 mL of 30% Acetonitrile/$H_2O$. 30 g resin (about 100 fold molar ratio to positive charges of the peptide) is added. The mixture solution is mixed by rotary stirring at room temperature for 1 hour. The mixture solution is filtered, and the resin is washed 5 times with 30% ACN/$H_2O$. The original solution and washed solution are combined and lyophilized.

Solubility and Chemical Stability

The compound of SEQ ID NO: 2 is dissolved in 20 mM Tris-HCl/$H_2O$, pH 8 to a 1 mg/mL concentration (peptide content), and filtered through a 0.22 micron filter (Millex, SLGV004SL). Solution is transferred to three vials: one for 4° C.; one for 30° C. and one for 40° C. All vials are autoclaved. Samples are visually assessed at different time points for turbidity and phase separation. Stability of the compound is assessed by analytical HPLC on a Phenomenex Aeris Widepore, 3.6 μm, XB-C18 4.6×250 mm column (P/NO 00G-4482-E0) heated at 60° C. with a AB (A=0.05% TFA/$H_2O$; B=0.04% TFA/acetonitrile) gradient of 5% B isocratic over 5 min, 5 to 30% B over 20 minutes, 30 to 35% B over 30 min, and 35% to 45% B over 10 min with a flow rate of 1.2 mL/min (wavelength of 220 ηm).

The compound of SEQ ID NO: 2 of the present invention maintains good solubility at 4° C., 30° C. and 40° C., in Tris-HCl buffer at pH8 in 4-wk both by visual assessment and by RP-HPLC.

TABLE 1

| pH | Total Peak Area day 0 | 4° C. Total Peak Area 4 wk | 30° C. Total Peak Area 4 wk | 40° C. Total Peak Area 4 wk | 30° C. vs 4° C. Recovery 4 wk | 40° C. vs 4° C. Recovery 4 wk |
|---|---|---|---|---|---|---|
| 8 | 4666 | 4418 | 4458 | 4393 | 101% | 99% |

The compound of SEQ ID NO: 2 maintains chemical stability at 4° C., 30° C. and 40° C., at pH 8 in 4-wk both by visual assessment and by RP-HPLC. RP-HPLC main peak changes: <2.5% (4-wk 30° C. vs 4° C.); <7% (4-wk 40° C. vs 4° C.) (see Table 2).

TABLE 2

| pH | % Main Peak Day 0 | 4° C. % Main Peak 4 wk | 30° C. % Main Peak 4 wk | 40° C. % Main Peak 4 wk |
|---|---|---|---|---|
| 8 | 96.26 | 95.94 | 93.73 | 89.54 |

Physical Stability Test Using Thioflavin T Binding Assay

Fibrillation is a common problem when glucagon is formulated in aqueous solution. To assess the level of fibrillation of the compound of the present invention, a Thioflavin T binding assay is performed.

The compound of SEQ ID NO: 2 is dissolved in various test buffers at 1 mg/mL in 2.5 mL Fisher vials with a flat bottom (Fisher FS60965D) containing a flea sized stirring bar (Fishers Catalog #1451364). Test buffers are prepared in $H_2O$ and are all adjusted to pH 8.0:
Buffer 1=20 mM Tris-HCl
Buffer 2=20 mM Tris-HCl, 150 nM NaCl
Buffer 3=20 mM Tris-HCl, 300 mM sucrose
Buffer 4=20 mM Tris-HCl, 300 mM sorbitol
Buffer 5=20 mM Tris-HCl, 0.02% Tween 80

In addition, human glucagon (SEQ ID NO: 1) is dissolved in a 12 mg/mL glycerol solution at pH 2.8 to a final concentration of 1 mg/mL. All samples are mechanically stressed at 25° C. in a magnetic stir plate set at 300 rpm. Aliquots of the different samples (100 μL each aliquot and done in triplicates) are taken at time points 0, 40 and 120 hours, and are added to a plate followed by 10 μL of a 1 mM Thioflavin T (stock solution in $H_2O$, pH 2.8) (T35516-25G, Sigma Aldrich). Samples are incubated for 30 min. Fluorescence is measured using a Spectramax M5 (Moleculer Devices) using 440 ηm as the excitation wavelength, and the emission wavelength is set at 480 ηm with a 475 ηm cut off and automatic sensitivity adjustment. Raw data is collected with Softmax Pro 5.4.1 (Molecular Devices) and imported to Excel. The average of the 3 wells per each time point becomes the reported flurescence units shown in Table 3 below:

TABLE 3

| Sample | t = 0 h | t = 40 h | t = 120 h |
| --- | --- | --- | --- |
| SEQ ID NO: 2 in Buffer 1 | 193.9 | 201.6 | 226.1 |
| SEQ ID NO: 2 in Buffer 2 | 182.2 | 210.1 | 213.6 |
| SEQ ID NO: 2 in Buffer 3 | 263.3 | 297.0 | 310.9 |
| SEQ ID NO: 2 in Buffer 4 | 260.9 | 285.1 | 311.2 |
| SEQ ID NO: 2 in Buffer 5 | 251.7 | 281.7 | 306.8 |
| Human glucagon (SEQ ID NO: 1) in 12 mg/mL glycerol, pH 2.8 | 37.1 | 462.7 | 737.1 |
| Buffer 1 | 32.4 | 32.5 | 36.5 |
| Buffer 2 | 33.6 | 44.2 | 34.6 |
| Buffer 3 | 46.4 | 47.4 | 50.5 |
| Buffer 4 | 38.8 | 38.4 | 38.2 |
| Buffer 5 | 33.1 | 35.2 | 35.0 |
| 12 mg/mL glycerol, pH 2.8 | 33.3 | 36.7 | 37.4 |

As shown in Table 3, the compound of SEQ ID NO: 2 maintains physical stability at 25° C. and pH 8 for 120 hours in the presence of mechanical stress as assessed by both visual assessment and Thioflavin T binding assays. The compound of SEQ ID NO: 2 did not demonstrate significant fibrillation as measured by the Thioflavin T binding assay.

Effects of Compound on Blood Glucose Levels in C57/B16 Male Mice

To determine the effects of the compound of SEQ ID NO: 2 on blood glucose levels, the compound is administered to C57/B 16 mice. Three month old male C57BL6 mice (Harlan Laboratories) are used Animals are individually housed in a temperature-controlled (24° C.) facility with a 12 hour light/dark cycle, and have free access to food and water. After 1 week acclimation to the facility, mice are randomized to treatment groups (n=4/group). Test compound is formulated in Buffer 2 (see Physical stability test using Thioflavin T binding assay). On the morning of test, food is removed at 08:00 AM. Two hours after food is removed, the test compound is given subcutaneously at 0, 1, 3 or 10 μg/kg doses. Blood glucose is measured at time 0, 15, 30, 60 and 120 minutes after test compound administration with an ACCU-CHECK® (Roche Diagnostics) glucometer. Table 4 shows the glucose values at different time points. Results are expressed as mean ±standard error mean (SEM) of 4 mice per group.

$ED_{50}$ is calculated on the 30 minute glucose measurements. Blood glucose levels at 10 μg/kg of compound of SEQ ID NO: 2 is taken as the maximum value. For the compound of SEQ ID NO: 2, the $ED_{50}$ is 3.34 μg/kg (95% confidence interval). The results demonstrate that the compound of SEQ ID NO: 2 is able to increase blood glucose.

TABLE 4

| Time (minutes) | Blood glucose levels (mg/dL) after dosing with compound of SEQ ID NO: 2 | | | |
| --- | --- | --- | --- | --- |
| | 0 μg/kg | 1 μg/kg | 3 μg/kg | 10 μg/kg |
| 0 | 134.1 ± 1.2 | 132.0 ± 4.1 | 147.8 ± 2.6 | 146.0 ± 8.2 |
| 15 | 151.1 ± 12.2 | 203.0 ± 15.8 | 246.4 ± 13.1 | 257.3 ± 7.7 |
| 30 | 171.8 ± 10.3 | 220.4 ± 21.4 | 274.9 ± 16.3 | 294.0 ± 13.3 |
| 60 | 166.9 ± 3.7 | 171.6 ± 10.2 | 201.1 ± 13.2 | 222.2 ± 13.9 |
| 120 | 164.0 ± 7.3 | 168.9 ± 3.7 | 172.8 ± 8.9 | 147.0 ± 6.7 |

Human Glucagon Receptor Binding Assay

The binding of the compound of SEQ ID NO: 2 is determined by using a 293HEK cell line overexpressing the human glucagon receptor (hGR) (Lok S et al. Gene 140 (2), 203-209 (1994); GenBank: L20316).

Crude plasma membranes are prepared using cells from suspension or adherent culture. The cell pellets are lysed on ice in a hypotonic homogenization buffer (25 mM Tris HCl, pH 7.5, 1 mM $MgCl_2$, and Roche Complete™ Inhibitors without EDTA (Roche, 11873580001)) with DNAase at 20 μg/ml (Invitrogen, 18047-019). The cell suspension is homogenized with a glass dounce homogenizer using a Teflon pestle for 25 strokes. The homogenate is centrifuged 1800× g at 4° C. for 15 min. The supernatant is collected and the pellet is resuspended in hypotonic homogenization buffer (without DNAse) and re-homogenized. The mixture is centrifuged at 1800× g for 15 min. The second supernatant is combined with the first supernatant and centrifuged at 1800× g for 15 min to clarify. This clarified supernatant is further centrifuged at 25000× g for 30 min at 4° C. The membrane pellet is resuspended in hypotonic homogenization buffer (without DNAse) and stored as frozen aliquots at −80° C. until use.

Human glucagon is radioiodinated by $^{125}$I-lactoperoxidase procedure and purified by reversed phase HPLC at Perkin-Elmer/NEN (NEX207). The specific activity is about 2200 Ci/mmol $K_D$ determination is performed by homologous competition instead of saturation binding due to high propanol content in the $^{125}$I-labelled glucagon material. The $K_D$ is estimated to be 1.24 ηM and is used to calculate Ki values for all compounds tested.

The receptor binding assay is carried out using a Scintillation Proximity Assay (SPA) (Sun, S., Almaden, J., Carlson, T. J., Barker, J. and Gehring, M. R. Assay development and data analysis of receptor-ligand binding based on scintillation proximity assay. *Metab Eng.* 7:38-44 (2005)) with wheat germ agglutinin (WGA) beads (Perkin-Elmer) previously blocked with 1% fatty acid free bovine serum albumin (BSA) (Gibco, 7.5% BSA) Human glucagon (SEQ ID NO:

1) and compound (SEQ ID NO: 2) are dissolved in dimethyl sulfoxide (DMSO) at a concentration of 2 mM and stored frozen at −20° C.

Human glucagon and compound of SEQ ID NO: 2 are serially diluted into DMSO. 10 μL of diluted samples are transferred into Corning 3632 clear bottom assay plates containing 40 μL assay Binding Buffer (25 mM 4-(2-hydroxyethyl)-1-piperazineethanesulfonic acid (HEPES), pH 7.4, 2.5 mM $CaCl_2$, 1 mM $MgCl_2$, 0.1% fatty acid free BSA, 0.003% Tween20, and Roche Complete Inhibitors without EDTA) or cold glucagon (non-specific binding (NSB) at 1 μM final). 90 μL membranes (3 μg/well), 50 μL $^{125}$I-labelled Glucagon (0.15 ηM final concentration in reaction), and 50 μL of WGA beads (150 μg/well) are added. DMSO concentration does not exceed 4.2%. Plates are sealed, mixed end over end, and read with a MicroBeta® scintillation counter after 12 hours of settling time at room temperature.

Results are calculated as a percent of specific $^{125}$I-labelled glucagon binding in the presence of compound. The absolute $IC_{50}$ concentration of compound is derived by non-linear regression of percent specific binding of $^{125}$I-labelled glucagon vs. the concentration of sample added ($8.5 \times 10^{-12}$ to $0.5 \times 10^{-7}$ mol/L). The $IC_{50}$ dose is converted to Ki using the Cheng-Prusoff equation (Cheng Y., Prusoff W. H., Biochem. Pharmacol. 22: 3099-3108 (1973)). The Ki of the compound of SEQ ID NO: 2 was 3.20±0.76 ηM (n=3) for hGR binding (Ki for human glucagon was 1.66±0.09 ηM (n=47) for hGR binding). This data demonstrates that the compound of SEQ ID NO: 2 binds to hGR with similar affinity compared to human glucagon and may activate that receptor, in turn triggering glucagon-dependent physiological responses.

Mouse Glucagon Receptor Binding Assay

To determine whether the compound of SEQ ID NO: 2 binds to the mouse glucagon receptor (mGR), a binding assay as essentially described in the Human Glucagon Receptor Binding Assay is performed. Crude plasma membranes are prepared from 293HEK cells in suspension culture expressing a cloned mGR. ((Burcelin R, Li J, Charron M J. Gene 164 (2), 305-10 (1995) GenBank: L38613). Membrane pellets are prepared as described in the Human Glucagon Receptor Binding Assay, resuspended in homogenization buffer and stored as frozen aliquots at −80° C. until use.

Human glucagon is radioiodinated by $^{125}$I-lactoperoxidase procedure and purified by reversed phase HPLC at Perkin-Elmer/NEN (NEX207). The specific activity is about 2200 Ci/mmol $K_D$ determination is performed by homologous competition instead of saturation binding due to high propanol content in the $^{125}$I-labelled glucagon material. The $K_D$ is estimated to be 2.05 ηM and is used to calculate Ki values for all compounds tested.

The SPA receptor binding assay and calculation of the results are carried out as described in the Human Glucagon Receptor Binding Assay. The Ki of the compound of SEQ ID NO: 2 was 8.63±0.71 ηM (n=3) for mGR binding (Ki for human glucagon was 1.37±0.07 ηM (n=33) for mGR binding). This data demonstrates that compound of SEQ ID NO: 2 binds to mGR and may activate that receptor, in turn triggering glucagon-dependent physiological responses.

Glucagon-Like-Peptide 1 Receptor Binding Assay

To determine whether the compound of SEQ ID NO: 2 binds to the human glucagon-like peptide 1 receptor (hGLP-1R), a binding assay as essentially described in the Human Glucagon Receptor Binding Assay is performed. Crude plasma membranes are prepared from 293HEK suspension cells expressing a cloned human glucagon-like peptide 1 receptor (hGLP-1R) (Graziano M P, Hey P J, Borkowski D, Chicchi G G, Strader C D, Biochem Biophys Res Commun. 196 (1):141-6 (1993) GenBank: NM_002062) isolated from 293HEK membranes. Membrane pellets are prepared as described in the Human Glucagon Receptor Binding Assay, resuspended in homogenization buffer and stored as frozen aliquots at −80° C. until use.

Glucagon-like peptide 1 7-36 amide (GLP-1 amide) (SEQ ID NO: 3) is radioiodinated by the $^{125}$I-lactoperoxidase procedure and purified by reversed phase HPLC at Perkin-Elmer/NEN (NEX308). The specific activity is about 2200 Ci/mmol $K_D$ determination is performed by homologous competition instead of saturation binding due to high propanol content in the $^{125}$I-labelled GLP-1 amide material. The $K_D$ is estimated to be 0.329 ηM and is used to calculate Ki values for all compounds tested.

The SPA receptor binding assay and calculation of the results are carried out as described in the Human Glucagon Receptor Binding Assay with the exception that radioiodinated GLP-1 amide is used instead of the radioiodinated glucagon of the Human Glucagon Receptor Binding Assay.

The Ki of the compound of SEQ ID NO: 2 was >3380 ηM (n=3) for hGLP-1R binding while the Ki of glucagon (SEQ ID NO:1) was 2098±91 (n=17) (Ki for human GLP-1 7-36 amide was 0.427±0.169 ηM (n=64) for hGLP-1R binding). This data demonstrates that the compound of SEQ ID NO: 2 does not specifically bind to hGLP-1R and thus does not initiate GLP-1R-mediated physiological responses.

Glucose-Dependent Insulinotropic Peptide Receptor Binding Assay

To determine whether the compound of SEQ ID NO: 2 binds to the glucose-dependent insulinotropic peptide receptor (GIP-R), a binding assay as essentially described in the Human Glucagon Receptor Binding Assay is performed. Crude plasma membranes are prepared from suspension Chinese Hamster Ovary cells (CHO-S) expressing human GIP-R (R (Usdin, T. B., Gruber, C., Modi, W. and Bonner, T. I., GenBank: AAA84418.1) using cells from suspension culture. Membrane pellets are prepared as described in the Human Glucagon Receptor Binding Assay, resuspended in homogenization buffer and stored as frozen aliquots at −80° C. until use.

GIP (SEQ ID NO: 4) is radioiodinated by the I-125-lactoperoxidase procedure (Markalonis, J. J., Biochem. J. 113:299 (1969)) and purified by reversed phase HPLC at Perkin-Elmer/NEN (NEX-402). The specific activity is 2200 Ci/mmol $K_D$ determination is performed by homologous competition using cold human GIP instead of saturation binding. The $K_D$ is estimated to be 0.174 ηM and is used to calculate Ki values for all compounds tested.

The SPA receptor binding assay and calculation of the results are carried out as described in the Human Glucagon Receptor Binding Assay The Ki of the compound of SEQ NO: 2 was >2240 ηM (n=1) for human GIP-R binding while the Ki of glucagon (SEQ ID NO: 1) was >3010 (n=1) (Ki for human GIP was 0.127±0.048 ηM). This data demonstrates that the compound of SEQ ID NO: 2 does not specifically bind to hGIP-R and thus does not initiate hGIP-R-mediated physiological responses.

Human Glucagon Receptor Stimulated cAMP Functional Assay.

The hGR stimulated cAMP functional assay uses the same cloned hGR expressing cell line as used for the hGR binding assay described above in the Human Glucagon Receptor Binding Assay. Cells are stimulated with glucagon, buffer controls, or Test samples, and the cAMP generated within the cell is quantitated using the CisBio cAMP Dynamic 2

HTRF Assay Kit (62AM4PEC). Briefly, cAMP levels within the cell are detected by binding to the cAMP-d2 capture antibody in the presence of cell lysis buffer. A second detection antibody provided in the kit, anti-cAMP Cryptate, is added to create a competitive sandwich assay. When the detection antibody complex formed there is an increase in the signal that is measured on a Perkin-Elmer Envision® instrument.

The hGR-HEK293 cells are harvested from sub-confluent tissue culture dishes with Enzyme-Free Cell Dissociation Solution (Specialty Media 5-004-B). The cells are pelleted at 100× g at room temperature for 5 minutes then washed twice with phosphate buffered saline (PBS). The washed cell pellet is resuspended at $1 \times 10^7$ cells/ml in Recovery™ Freeze Media (Gibco 2044) and frozen in liquid nitrogen. On the day of treatment, a frozen aliquot of cells is transferred into pre-warmed Resuspension Cell Media (DMEM, Gibco (31053P) containing 0.5% defined FBS (Hyclone SH30070); 20 mM HEPES, pH 7.4; and 2 mM Glutamine). The cells are then pelleted at 100× g at room temperature for 5 minutes. The supernatant is removed and the cell pellet is resuspended in Cell Media (DMEM, Gibco (31053P) with 0.1% fatty acid-free bovine serum albumin, BSA, 7.5%, (Gibco 15620); 20 mM HEPES, pH 7.4, and 2 mM Glutamine) at $1.25 \times 10^5$ cells/ml. Test samples are prepared as 2 mM stocks in DMSO and frozen at −20° C. until needed. Glucagon, buffer controls and compound of SEQ ID NO: 2, are serially diluted into DMSO followed by a step-down dilution into Compound Dilution Media (Assay Media (DMEM, Gibco 31053P with 0.1% fatty acid-free bovine serum albumin, BSA, 7.5%, (Gibco 15620); 20 mM HEPES, pH 7.4, and 2 mM Glutamine) that contains 500 µM IBMX). The reaction is performed in 40 µL, by adding 20 µL of cells (2500 cell/well) or cAMP standard curve samples to 96 Well plate Half Area Black plates (Costar 3694), followed by addition of 20 µL of either 2X concentrated glucagon, buffer controls or compound of SEQ ID NO: 2 in Compound Dilution Media. Final DMSO concentration does not exceed 1.1%, and final IBMX concentration is 250 µM. The reaction is stopped by addition of 20 µL of the cAMP-d2-capture antibody (CisBio) diluted into the CisBio lysis buffer then gently mixed in TITERTEK shaker. After 5 minutes of lysis, 20 µL of the detection antibody, anti-cAMP Cryptate (CisBio), is added and mixed at 600 rpm for 1 minute. The lysed cell and antibody mixtures are read after 1 hour at room temperature using the Perkin-Elmer Envision®. Envision® units were converted to pmol/L cAMP/well using the cAMP standard curve. The picomoles of cAMP generated in each well is converted to a percent of the maximal response observed with the glucagon control. A relative $EC_{50}$ value is derived by non-linear regression analysis using the percent maximal response vs. the concentration ($0.17 \times 10^{-12}$ to $1 \times 10^{-8}$ M) of peptide added.

The compound of SEQ ID NO: 2 bound hGR with an $EC_{50}$ of $0.0658 \pm 0.0167$ ηM (n=8) ($EC_{50}$ for human glucagon was $0.0142 \pm 0.0018$ ηM (n=6)). This data demonstrates that the compound of SEQ ID NO: 2 binds and activates hGR and can thereby initiate glucagon receptor-mediated physiological responses.

---

Sequence Listing

Human glucagon:
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr (SEQ ID NO: 1)

Example 1:
Tyr-Ser-His-Gly-Thr-Phe-Thr-Ser-Asp-Val-Ser-Lys-

Tyr-Leu-Asp-(Aib)-Lys-Lys-Ala-Ala-Glu-Phe-Val-

Ala-Trp-Leu-Leu-Glu-Glu (SEQ ID NO: 2)

Human GLP-1:
His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Arg-NH$_2$ (SEQ ID NO: 3)

Human GIP:
Tyr-Ala-Glu-Gly-Thr-Phe-Ile-Ser-Asp-Tyr-Ser-Ile-

Ala-Met-Asp-Lys-Ile-His-Gln-Gln-Asp-Phe-Val-Asn-

Trp-Leu-Leu-Ala-Gln-Lys-Gly-Lys-Lys-Asn-Asp-Trp-

Lys-His-Asn-Ile-Thr-Gln (SEQ ID NO: 4)

---

We claim:

1. A compound comprising the amino acid sequence of Tyr-Ser-His-Gly-Thr-Phe-Thr-Ser-Asp-Val-Ser-Lys-Tyr-Leu-Asp-(Aib)-Lys-Lys-Ala-Ala-Glu-Phe-Val-Ala-Trp-Leu-Leu-Glu-Glu (SEQ ID NO: 2).

2. The compound of claim 1, wherein the compound consists of the amino acid sequence of Tyr-Ser-His-Gly-Thr-Phe-Thr-Ser-Asp-Val-Ser-Lys-Tyr-Leu-Asp-(Aib)-Lys-Lys-Ala-Ala-Glu-Phe-Val-Ala-Trp-Leu-Leu-Glu-Glu (SEQ ID NO: 2).

3. A pharmaceutical composition comprising the compound of claim 1 and a pharmaceutically acceptable buffer.

4. The pharmaceutical composition of claim 3, wherein the pharmaceutically acceptable buffer is histidine-buffered saline.

5. A pharmaceutical composition comprising the compound of claim 2 and a pharmaceutically acceptable buffer.

6. The pharmaceutical composition of claim 5, wherein the pharmaceutically acceptable buffer is histidine-buffered saline.

7. A method of treating hypoglycemia in a subject comprising administering an effective amount of a compound of claim 1.

8. A method of treating hypoglycemia in a subject comprising administering an effective amount of a compound of claim 2.

* * * * *

UNITED STATES PATENT AND TRADEMARK OFFICE
CERTIFICATE OF CORRECTION

PATENT NO. : 9,688,736 B2
APPLICATION NO. : 15/103169
DATED : June 27, 2017
INVENTOR(S) : Jorge Alsina-Fernandez et al.

Page 1 of 1

It is certified that error appears in the above-identified patent and that said Letters Patent is hereby corrected as shown below:

On the Title Page

Item (54) and in the Specification, in Column 1, Line 1 (title), before "COMPOUND" insert --A PEPTIDE--.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 4

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa at position 16 is 2-aminoisobutyric acid

<400> SEQUENCE: 2

Tyr Ser His Gly Thr Phe Thr Ser Asp Val Ser Lys Tyr Leu Asp Xaa
1               5                   10                  15

Lys Lys Ala Ala Glu Phe Val Ala Trp Leu Leu Glu Glu
            20                  25

<210> SEQ ID NO 3
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 42
<212> TYPE: PRT
<213> ORGANISM: Homo sapiens

<400> SEQUENCE: 4

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40
```